United States Patent
Leonhardt et al.

(10) Patent No.: US 7,162,296 B2
(45) Date of Patent: Jan. 9, 2007

(54) VENTILATION SYSTEM

(75) Inventors: Steffen Leonhardt, Lübeck (DE); Eckhard Teschner, Hamburg (DE)

(73) Assignee: Dräger Medical AG & Co KGaA (DE)

( * ) Notice: Subject to any disclaimer, the term of this patent is extended or adjusted under 35 U.S.C. 154(b) by 399 days.

(21) Appl. No.: 10/742,356

(22) Filed: Dec. 18, 2003

(65) Prior Publication Data

US 2004/0133123 A1 Jul. 8, 2004

(30) Foreign Application Priority Data

Dec. 21, 2002 (DE) ............... 102 60 448
Jan. 15, 2003 (DE) ............... 103 01 202

(51) Int. Cl.
*A61B 5/02* (2006.01)
*A61B 5/05* (2006.01)
*A61M 16/00* (2006.01)
*A62B 7/00* (2006.01)
*F16K 31/02* (2006.01)

(52) U.S. Cl. .............. 600/547; 600/529; 128/204.23
(58) Field of Classification Search ............ 600/547, 600/529–543, 546; 128/204.23, 202.22
See application file for complete search history.

(56) References Cited

U.S. PATENT DOCUMENTS 6,723,055 B1* 4/2004 Hoffman ............... 600/538

2003/0216664 A1* 11/2003 Suzrez ............... 600/547

FOREIGN PATENT DOCUMENTS

EP  1 000 580 A1  5/2000

OTHER PUBLICATIONS

Kunst, A.W. et al, Monitoring of recruitment and derecruitment by electrical impedance tomography in a model of acute lung injury, Critical Care Medicine, vol. 28(12): 3891-3895, 2000.*

Frerichs et al., Monitoring Regional Lung Ventilation by Functional Electrical Impedance Tomography during Assisted Ventilation, Annals of the New York Academy of Sciences, vol. 873, pp. 493-505, 1999.*

* cited by examiner

Primary Examiner—Robert L. Nasser
(74) Attorney, Agent, or Firm—McGlew & Tuttle, PC

(57) ABSTRACT

A ventilation system (1, 10) is combined with a measuring method (2, 22, 222) for electric impedance tomography (EIT). Bidirectional data exchange between the two systems is provided. Both the ventilation system (1, 10) and the measuring system (2, 22, 222) have a first and second communications electronic unit (11, 12) each with associated transmitting and receiving means for the bidirectional data exchange.

27 Claims, 3 Drawing Sheets

VENTILATION SYSTEM

FIELD OF THE INVENTION

The present invention pertains to a ventilation system with a measuring system for electric impedance tomography.

BACKGROUND OF THE INVENTION

Electric impedance tomography (EIT) is a noninvasive method, which is known per se, in which an alternating current of a few mA with a frequency of, e.g., 50 kHz is fed into an electrically conductive body, especially the human body, and the resulting surface potentials are measured at different points of the body. Based on mathematical reconstruction algorithms, which are known per se, a two-dimensional tomogram of the electric impedance distribution can be determined in the body being examined by the successive rotation of the current feed points around the body while measuring the surface potentials at the same time along a section plane. Such a tomogram of the impedance distribution of the human body is of interest in medicine, because the electric impedance changes both with the air content and with the extracellular fluid content in the tissue. Both the ventilation of the lungs and the shifts in the blood and serum due to physiological changes can thus be displayed in a locally resolved manner and monitored.

A known measuring system for electric impedance tomography is described in EP 1 000 580 A1, in which the graphic display of the measured impedance values is superimposed by the display of an imaging system for the same body slice in order to make possible a more accurate evaluation of the measurements performed by means of electric impedance tomography.

SUMMARY OF THE INVENTION

The object of the present invention is to provide a device for monitoring the mechanical ventilation of a patient, which is performed by means of a ventilation system/respiration system (with a respirator/ventilator).

According to the invention, a ventilation system (respiration system) is combined with a measuring system for electric impedance tomography. The system includes a means for bidirectional data exchange between the ventilation system and the measuring system for the electric impedance tomography.

An essential advantage of the present invention is that, on the one hand, the measurement at the patient can be performed at exactly defined points in time and depending on the ventilation pattern due to the bidirectional data exchange between the ventilation system and the measuring system for the electric impedance tomography and, on the other hand, current measured signals, which are used for the display of the current state and/or for controlling the ventilation system, are transmitted to the ventilation system as a function of the measurement at the patient.

An electric wire connection may be present as a means for the bidirectional data exchange between the ventilation system and the measuring system. The ventilation system and the measuring system may have a first and second communications electronic unit each with transmitting and receiving means as means for the wireless bidirectional data exchange. The bidirectional data exchange may be performed by means of a directional radio link or an infrared transmission link.

The measured impedance data may be transmitted by the measuring system to the ventilation system. The impedance data measured in a time-dependent manner may be separated by means of at least one filter in a frequency-dependent manner. An adaptive high-pass filter or band pass filter may be used to separate the impedance data relevant for the cardiac activity, and an adaptive low pass filter or band pass filter may be used to separate the impedance data relevant for the pulmonary or respiratory activity.

The measuring system may determine the current heart rate from the impedance data and transmit it to the ventilation system.

The measuring system may be activated depending on the ventilation pattern and/or the measured pressure or volume flow in the ventilation system so that impedance data, which will be used as reference values for the impedance measurement that follow in time, are determined at predetermined points in the ventilation pattern. The ventilation system may be controlled by the measuring system as a function of the measured impedance data and after comparison with stored reference values. Acoustic and/or optical alarm triggering units may be present, so that an acoustic and/or optical alarm is triggered in the ventilation system by the measuring system when actual values drop below or exceed limit values of the electric impedance which are stored in the ventilation system or in the measuring system.

The measuring system may have a plurality of electrodes El through En, which are arranged especially in an electrode belt with an analog connection line to an analog-digital interface circuit and with an adjoining first digital connection line, which is connected to a monitor of the measuring system. The measuring system may be connected via the electric wire connection to the ventilation system.

The measuring system may also have a plurality of electrodes El through En arranged especially in an electrode belt with an analog connection line to an analog-digital interface circuit with an adjoining electric wire connection, which is connected to an interface card of a ventilation system thus expanded, which said interface card contains evaluation and control functions of the measuring system.

A measuring system may have a plurality of electrodes El through En arranged especially in an electrode belt with an analog connection line to an analog-digital interface circuit with an adjoining first digital connection line. The first digital connection line may be connected to the first communications electronic unit of the measuring system with the transmitting and receiving means, which may be connected to the second communications electronic unit of the ventilation system.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated. The same parts are designated in all figures by identical reference numbers.

DESCRIPTION OF THE PREFERRED EMBODIMENTS

Figure 1:
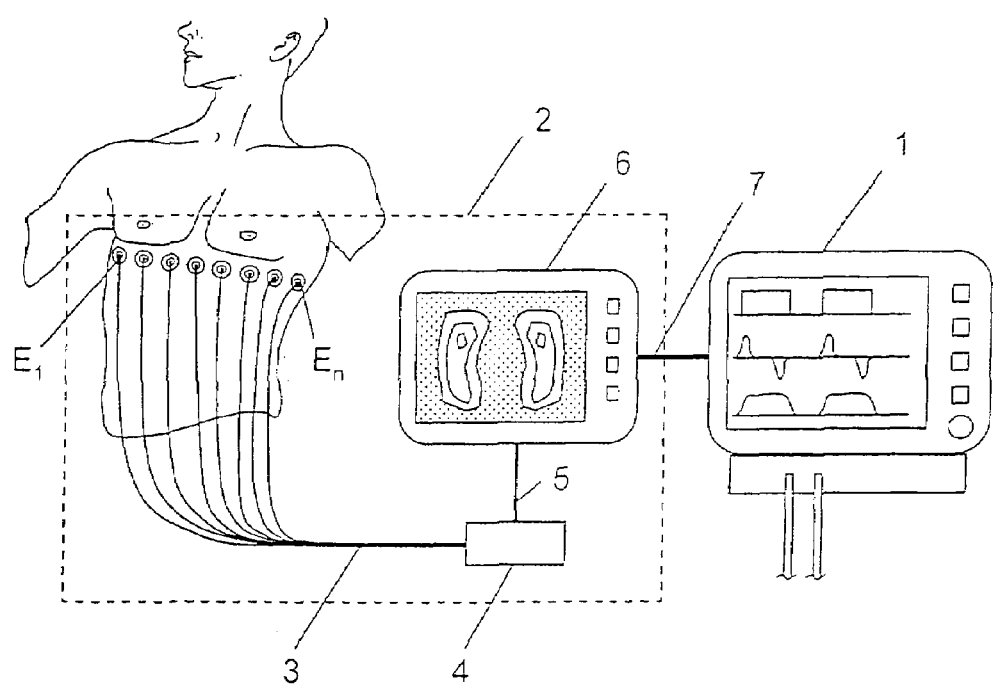
FIG. 1 is a schematic view of a first exemplary embodiment of the present invention with an electric cable connection between a ventilation system and a measuring system for the electric impedance tomography.

Referring to the drawings in particular, FIG. 1 shows an external first measuring system 2 for the electric impedance tomography (EIT for short), which is connected to a ventilation system 1 by means of an electric wire connection 7. This electric connection is used for the bidirectional data exchange and optionally for the power supply for the EIT measuring system 2. The EIT measuring system 2 has a plurality of electrodes El through En, especially 16 or 32 electrodes, which are connected especially equidistantly in a section plane to the surface of the patient's chest, and which are preferably arranged in an electrode belt. One electrode pair each, switched in a circulating manner, is used to feed a weak alternating current of a few mA, while the respective other electrodes are used for the measurement of the surface potentials in order to ultimately calculate the impedance distribution in the body relative to the section plane of the electrodes.

The electrodes El through En are connected by means of the analog connection line 3 to the analog-digital interface circuit (interface) 4, which contains, in general, power sources, measuring amplifiers, analog-digital and digital-analog converters as well as computing units. The interface 4 is connected by means of the first digital connection line 5 to the monitor 6 of the EIT measuring system 2, so that the impedance values can be displayed on the display screen. The displays reveal locally resolved and time-resolved shifts in the blood and serum, so that physiological changes in the patient can be detected and optionally monitored.

The ventilation system 1 shown schematically is used to ventilate a patient and has, in general, a breathing gas metering unit and/or a breathing gas delivery means and measuring and control means in order to ventilate the patient according to a preset, stored ventilation pattern, e.g., in a pressure-controlled or volume-controlled manner. Data can be exchanged bidirectionally between the EIT measuring system 2 and the ventilation system 1 by means of the electric wire connection 7. For example, impedance data can thus be transmitted from the EIT measuring system 2 to the ventilation system 1.

The electric wire connection 7 preferably has a standardized interface component each, e.g., Ethernet interface (i.e., Carrier Sense Multiple Access/Collision Detection (CSMA/CD) IEEE 802.3 and ISO8802.3), in both the EIT measuring system 2 and the ventilation system 1.

Figure 2:
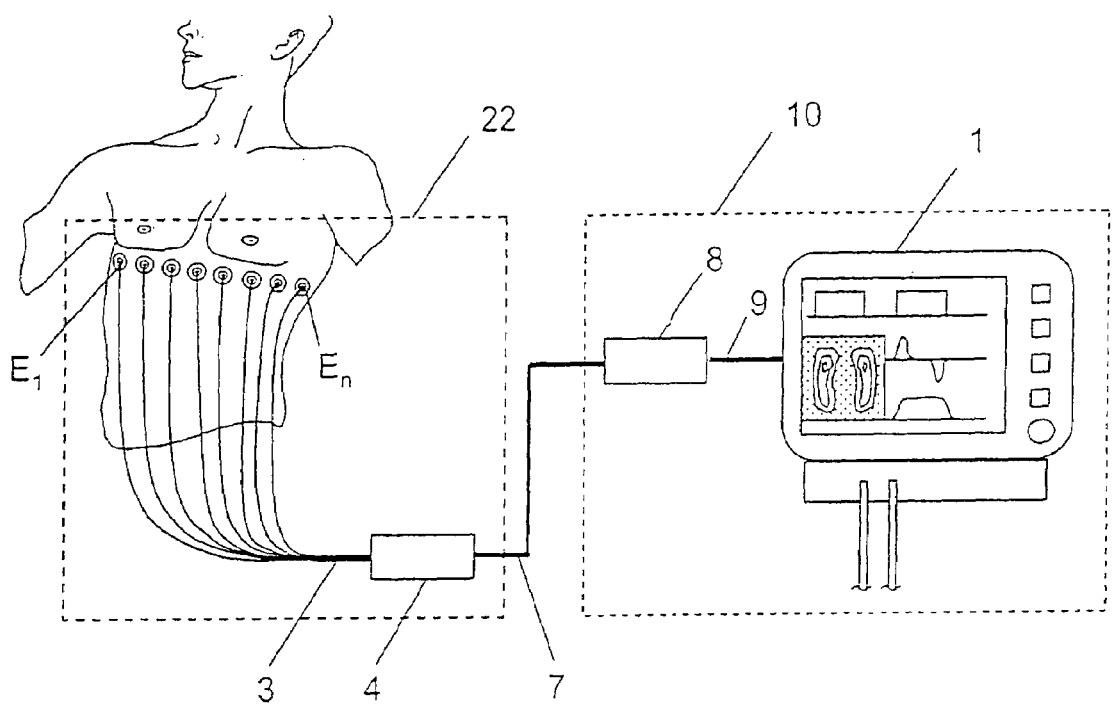
FIG. 2 is a schematic view of a second exemplary embodiment of the present invention with a measuring system for the electric impedance tomography, which measuring system is functionally extensively integrated within the ventilation system.

FIG. 2 shows a ventilation system 1 according to FIG. 1 integrated with an interface card 8 into an expanded ventilation system 10. The EIT functionalities in the exemplary embodiment according to FIG. 1 are provided in a second EIT measuring system 22. These functionalities are analyzing and control functionalities. The interface card 8 is either connected to the ventilation system 1 proper by means of the second digital connection line 9 or is completely integrated in the ventilation system 1. The communication within the expanded ventilation system 10 takes place, e.g., via Ethernet communication. The embodiment according to FIG. 2 has, just as the embodiment according to FIG. 3, only one monitor, namely, on the side of the ventilation system 1.

The time-resolved impedance curves measured by the second or third EIT measuring system 22 or 222, the impedance tomograms as well as the information derived therefrom are therefore displayed on the display screen of the ventilation system 1. This leads to cost and space savings as well as to a reduction in the energy consumption of the combination.

Figure 3:
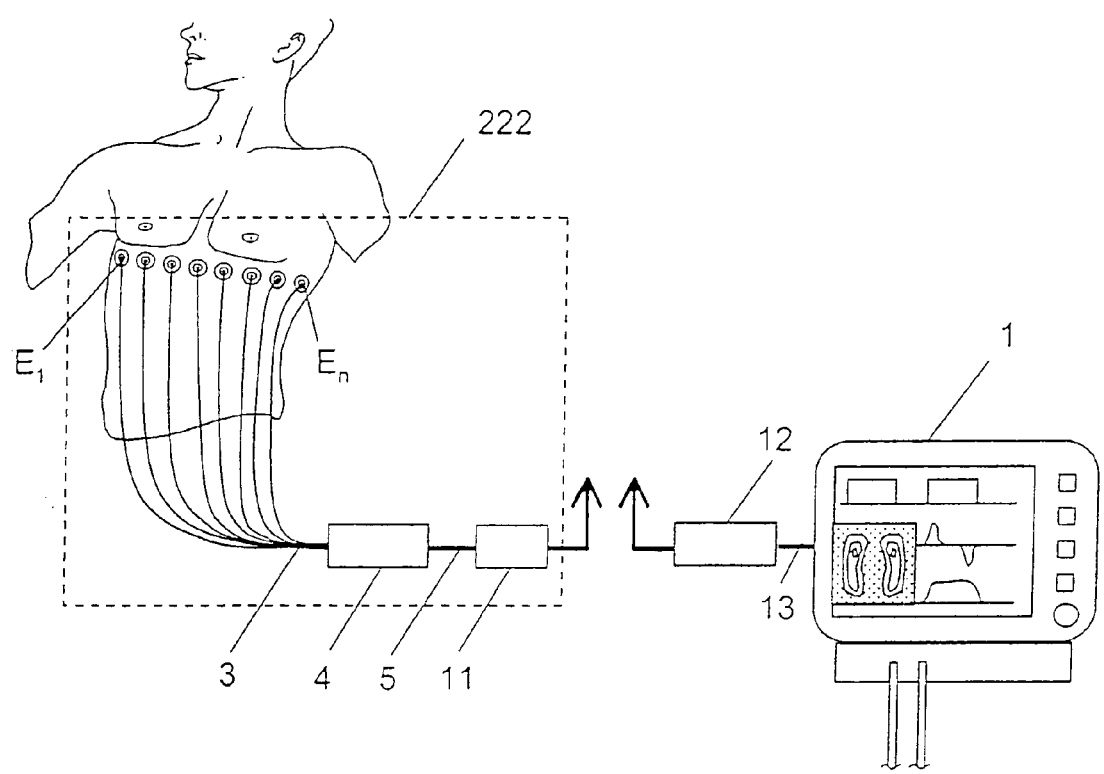
FIG. 3 is a schematic view of a third exemplary embodiment of the present invention with wireless transmitting and receiving means not bound to wires in the ventilation system and in the measuring system for the electric impedance tomography.

The embodiment according to FIG. 3 has a first communications electronic unit 11 with a transmitting and receiving means belonging to it on the side of the third EIT measuring system 222 as well as a second communications electronic unit 12 with a transmitting and receiving means belonging to it on the side of the ventilation system 1, so that a bidirectional data exchange can likewise take place with this arrangement. The second communications electronic unit 12 is either connected to the ventilation system 1 proper by means of the third digital connection line 13 or is completely integrated within the ventilation system 1. The second communications electronic unit 12 additionally contains EIT functionalities of the interface card 8 according to FIG. 2. The third EIT measuring system 222, containing the analog connection line 3 with the electrodes El through En, the analog-digital interface circuit 4, the first communications electronic unit 11 with transmitting and receiving means and the first digital connection line 5 belonging to it is preferably accommodated in this embodiment in a compact housing near the patient, especially bonded to the abdominal wall or is integrated in an electrode belt. The energy supply for the third EIT measuring system 222 is preferably ensured in this case via a battery-supplied power source. The wireless data transmission of the embodiment according to FIG. 3, preferably by means of infrared transmission or by means of an electromagnetic directional radio link, especially also according to the "Bluetooth" transmission standards (also IEEE 802.11a, b and g), has the advantage that the handling and care of the patient is substantially facilitated.

In a preferred application, the impedance signals are filtered by the EIT measuring system 2, 22, 222 in the time range by means of adaptive high-pass/low-pass filters or band pass filters, and only the filtered impedance signals are transmitted to the ventilation system 1. The filtering is designed such that low-frequency components of the frequency in the range of the ventilation can be separated from higher-frequency components of the frequency in the range of the heart rate. The current, patient-specific ventilation and heart rates are determined for this purpose and used to adapt the filter coefficients. The information obtained on the cardiac activity after frequency-selective filtering can be used, e.g., to monitor the heart and/or the pulmonary perfusion; in particular, alarms can be generated when the actual values exceed or drop below limit values set by the user. Such an alarm is, e.g., the "embolism" alarm, which reports a locally reduced pulmonary perfusion.

Another advantage of the filtering of the impedance signals is the possibility of monitoring the effect of the artificial ventilation on the heart and on the pulmonary perfusion. The ventilation parameters set by the user on the ventilation system 1, e.g., the ventilation volume, the ventilation pressures, the ventilation frequency or measured variables determined by the ventilation system 1, e.g., the end expiratory flow, are set for this purpose into relationship to the tomograms generated by the EIT measuring system 2, 22, 222, which were calculated from the impedance data in the frequency band of the cardiac activity. The effect of the artificial ventilation on the heart or on the pulmonary perfusion can also be monitored by the joint display of this information or of variables derived therefrom in the sense of a trend analysis. When actual values exceed or drop below certain limit values set by the user, the ventilation system 1 can trigger an alarm or automatically adapt the ventilation parameters.

Conversely, the EIT measuring system 2, 22, 222 may be activated by the ventilation system 1, e.g., as a function of the measured ventilation pattern, so that impedance data that will be used as reference values for impedance measurements performed later in time are determined by the EIT measuring system 2, 22, 222 at certain, predetermined points in the ventilation pattern, e.g., at the end of an expiration.

The ventilation system 1 may also be controlled automatically by the EIT measuring system 2, 22, 222 as a function of the measured impedance data and after comparison with stored reference values.

Not only data on the course of the ventilation over time, but also the scaling of displayed data over time, such as ventilation pressure or breathing gas volume flow, can be transmitted by the ventilation system 1 to the EIT measuring system 2, 22, 222. As a result, impedance data can be displayed on the monitor 8 in the embodiment according to FIG. 1 or on the display screen of the ventilation system I in the embodiment according to FIG. 2 or 3 in the same time resolution and synchronously in time with the ventilation data, so that the attending physician can establish a relationship between data from the ventilation system 1 and those from the EIT measuring system 2, 22, 222 in a simple form.

The ventilation of a patient can also be monitored by means of a device according to FIGS. 1 through 3: The ventilation system 1 reports the start of the ventilation to the EIT measuring system 2, 22, 222 and triggers the start of the impedance measurements there. It is possible, in particular, that the ventilation system 1 interrupts the ventilation cycle and maintains a constant airway pressure as a result (the so-called "inspiratory hold" during the inspiration, and the so-called "expiratory hold" during the expiration). Later on, the EIT measuring system 2, 22, 222 determines the ventilation that arises in the lungs, e.g., by the evaluation of the course of the local impedance changes over time or the integral of the impedance changes, and reports the result back to the ventilation system 1. If the result exceeds or drops below a certain, preset reference value, the EIT measuring system 2 or the ventilation system 1 may trigger an alarm.

Old impedance tomograms or data sets and corresponding ventilation settings can likewise be stored in the combination according to the present invention and compared with current impedance tomograms or data sets and corresponding ventilation settings in the sense of a trend analysis.

The system presents the advantages that this use permits the monitoring of the trend in the regional ventilation. E.g., it may happen that certain regions of the lung undergo changes in terms of their mechanical properties in the course of an artificial ventilation and are not ventilated any longer (atelectases).

Furthermore, a mucus plug formed over time may completely or partially close the airways and make bronchial suction of the airways necessary. The EIT measuring system 2, 22, 222 or the ventilation system 1 can trigger an alarm, e.g., an "Aspiration" or "Atelectases" alarm in these situations.

In another embodiment, the EIT measuring system 2, 22, 222 is designed such that regional pZ diagrams (in which p=airway pressure, Z=impedance), i.e., the display of local impedance values with corresponding airway pressure values, can be automatically obtained during an inspiration and/or expiration. The airway pressure p is plotted here against the impedance or impedance change for a local tomogram position or for the impedance or impedance change averaged over the entire tomogram.

This variant has the following advantages that assuming that the local impedance change in the impedance tomogram corresponds to a regional change in ventilation, the physician obtains as a result the possibility of evaluating regional pressure/volume diagrams in order to thus obtain information on the mechanical properties of the individual regions of the lung.

In an especially preferred embodiment, this variant is coupled with the generation of "slow inflation" maneuvers by the ventilation system 1. According to the definition, a "slow inflation" manoeuver is a process in which the lung of a patient being ventilated is slowly filled with air. This process takes place so slowly that it can be considered to be quasi-stationary from the viewpoint of the mechanical time constants of the lung. The combination offers the following advantage: assuming that the impedance change approximately corresponds to a local ventilation, regional "lower and upper inflection points" can be determined and read based on the pZ diagrams. These points characterize certain mechanical properties of the lung tissue, e.g., the incipient opening and the incipient overexpansion of alveoli.

In another embodiment, it is possible to monitor the intubation due to the combination of the EIT measuring system 2, 22, 222 and the ventilation system 1.

In the combination according to the present invention, the ventilation system 1 reports for this purpose the start of the ventilation to the EIT measuring system 2, 22, 222 and triggers the start of impedance measurements there. The EIT measuring system 2, 22, 222 determines the ventilation occurring in the lungs, e.g., based on the evaluation of certain local impedance changes over time or the global integral of the impedance changes, and it reports the result back to the ventilation system 1. If the measured result drops below a certain limit value as a consequence of an inadvertent intubation of the esophagus, the EIT measuring system 2, 22, 222 or the ventilation system 1 can trigger an alarm. This presents the advantage that it may happen especially in time-critical emergency situations that the esophagus is intubated and subsequently ventilated by mistake instead of the trachea. In situations in which the seating of the tube cannot be checked by means of a stethoscope, e.g., during transportation in a helicopter, the success of the intubation can be automatically monitored with the EIT measuring system 2, 22, 222.

While specific embodiments of the invention have been shown and described in detail to illustrate the application of the principles of the invention, it will be understood that the invention may be embodied otherwise without departing from such principles.

What is claimed is:
1. A system comprising:
   a ventilation system;
   a measuring system for performing electric impedance tomography, said measuring system measuring impedance data during the electric impedance tomography in a time-dependent manner and transmitting the data to said ventilation system;
   a filter separating the impedance data in a frequency-dependent manner; and communication means for bidirectional data exchange between said ventilation system and said measuring system for the electric impedance tomography.

2. A system in accordance with claim 1, wherein said communication means for the bidirectional data exchange between the ventilation system and the measuring system comprises an electric wire connection.

3. A system in accordance with claim 1, wherein said ventilation system includes a first communications electronic unit with transmitting and receiving means for the wireless bidirectional data exchange and said measuring system has a second communications electronic unit with transmitting and receiving means for the wireless bidirectional data exchange.

4. A system in accordance with claim 3, wherein the bidirectional data exchange is performed by means of a directional radio link or an infrared transmission link.

5. A system in accordance with claim 1, wherein said filter is an adaptive high-pass filter or band pass filter is used to separate the impedance data relevant for cardiac activity, and an adaptive low pass filter or another band pass filter is used to separate the impedance data relevant for pulmonary or respiratory activity.

6. A system in accordance with claim 5, wherein the measuring system determines the current heart rate from the impedance data and transmits it to the ventilation system.

7. A system in accordance with claim 1, wherein the measuring system includes:
a plurality of electrodes E1 through En, which are arranged in an electrode belt form;
an analog connection line to an analog-digital interface circuit with an adjoining first digital connection line;
a monitor connected to said adjoining first digital connection line, said electric wire connection connecting said measuring system to the ventilation system.

8. A system in accordance with claim 1, wherein the measuring system
includes:
a plurality of electrodes arranged in a belt form;
an analog connection line to an analog-digital interface circuit with an adjoining electric wire connection and wherein said ventilation system includes:
an interface card connected to said electric wire connection, said interface card including evaluation and control functions of the measuring system.

9. A system in accordance with claim 1, wherein the measuring system includes:
a plurality of electrodes arranged in a belt form and with an analog connection line to an analog-digital interface circuit with an adjoining first digital connection line;
a first communications electronic unit with a transmitter and a receiver and said ventilation unit includes:
a second communications electronic unit with a transmitter and receiver.

10. A system in accordance with claim 1, further comprising:
a display connected to said ventilation system and said measuring system for simultaneously displaying tomograms and the impedance data from the measuring system and displaying ventilation data from the ventilation system.

11. A system in accordance with claim 10, wherein:
said display provides diagrams comparing the impedance data with ventilation data.

12. A method of monitoring a patient during ventilation, the method comprising the steps of:

providing a ventilator and connecting it to a patient and initiating respiration;
providing an electric impedance tomography measurement system and connecting it to the same patient and measuring with the electric impedance tomography measurement system, said measuring being activated depending on a ventilation pattern and/or a measured pressure or volume flow in the ventilator so that impedance data, which will be used as reference values for the impedance measurement that follow in time, are determined at predetermined points in the ventilation pattern; and
providing bidirectional data exchange between the ventilator and the measuring system.

13. A method in accordance with claim 12, wherein said ventilator is connected to a first communications electronic unit with transmitting and receiving means for the wireless bidirectional data exchange and said measuring system has a second communications electronic unit with transmitting and receiving means for the wireless bidirectional data exchange.

14. A method in accordance with claim 13, wherein the bidirectional data exchange is performed by means of a directional radio link or an infrared transmission link.

15. A method in accordance with claim 13, wherein measured impedance data are transmitted by the measuring system to the ventilator.

16. A method in accordance with claim 15, wherein the impedance data measured in a time-dependent manner are separated by means of at least one filter in a frequency-dependent manner.

17. A method in accordance with claim 16, wherein an adaptive high-pass filter or band pass filter is used to separate the impedance data relevant for cardiac activity, and an adaptive low pass filter or band pass filter is used to separate the impedance data relevant for pulmonary or respiratory activity.

18. A method in accordance with claim 17, wherein the measuring method determines the current heart rate from the impedance data and transmits it to the ventilation method.

19. A method in accordance with claim 12, wherein the ventilation is controlled by the measuring system as a function of the measured impedance data and after comparison with stored reference values.

20. A method in accordance with claim 19, wherein acoustic and/or optical alarm triggering units are present, so that an acoustic and/or optical alarm is triggered in the ventilator by the measuring system when actual values drop below or exceed limit values of the electric impedance which are stored in the ventilation method or in the measuring method.

21. A method in accordance with claim 12, wherein said measuring includes attaching a plurality of electrodes to the patient, providing an analog connection line to an analog-digital interface circuit with an adjoining first digital connection line and using a monitor connected to said adjoining first digital connection line to monitor the patient and said bidirectional data exchange includes one of:
transferring data over an electric wire connection between said measuring system and the ventilator;
transferring data over an electric wire connection via an interface card of the ventilator connected to said electric wire connection, said interface card receiving evaluation and control functions of the measuring method; and
transferring data via a first communications electronic unit with a transmitter and a receiver connected to the measuring system and a second communications electronic unit with a transmitter and receiver connected to the ventilator.

22. A method of monitoring a patient during ventilation, the method comprising the steps of:
providing a ventilator and connecting it to a patient and initiating respiration;
providing an electric impedance tomography measurement system connected to the patient and measuring electric impedance data with the electric impedance tomography measurement system in a time-dependent manner;
separating impedance data by an adaptive high-pass filter or band pass filter to separate the impedance data relevant for cardiac activity, and by an adaptive low pass filter or band pass filter to separate the impedance data relevant for pulmonary or respiratory activity;
determining a current heart rate from the impedance data and transmitting the hear rate to the ventilator;
providing bidirectional data exchange between the ventilator and the measuring system.

23. A system comprising:
a ventilation system;
a measuring system for performing electric impedance tomography, said measuring system determining a current heart rate from data collected during the electric impedance tomography and transmitting the data to said ventilation system;
communication means for bidirectional data exchange between said ventilation system and said measuring system for the electric impedance tomography.

24. A system comprising:
a ventilation system;
a measuring system for electric impedance tomography, said measuring system being activated depending on a ventilation pattern and/or a measured pressure or volume flow in said ventilation system so that impedance data, which will be used as reference values for an impedance measurement that follows in time, are determined at predetermined points in the ventilation pattern;
communication means for bidirectional data exchange between said ventilation system and said measuring system for the electric impedance tomography.

25. A system in accordance with claim 24, wherein the ventilation system is controlled by the measuring system as a function of the measured impedance data and after comparison with stored reference values.

26. A system in accordance with claim 25, wherein acoustic and/or optical alarm triggering units are present, so that an acoustic and/or optical alarm is triggered in the ventilation system by the measuring system when actual values drop below or exceed limit values of the electric impedance which are stored in the ventilation system or in the measuring system.

27. A system comprising:
a measuring system for performing electric impedance tomography, said measuring system measurement system including a plurality of electrodes El to En, which are connected by an analog connection lead to an analog-digital adapter circuit;
communication means connected to said measuring system for bidirectional data exchange to and from said measuring system;
a ventilation system connected communication means for bidirectional data exchange between said ventilation system and said measuring system, said ventilation system including evaluating data from said measuring system and controlling said measuring system.

* * * * *